(12) United States Patent
Willard et al.

(10) Patent No.: US 10,646,325 B2
(45) Date of Patent: May 12, 2020

(54) STENT MIGRATION DEVICE AND METHOD

(71) Applicant: Medtronic Vascular, Inc., Santa Rosa, CA (US)

(72) Inventors: Martin Willard, Burnsville, MN (US); Benjamin J. Breit, Edina, MN (US); James Griffin, Evanston, IL (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 121 days.

(21) Appl. No.: 15/927,118

(22) Filed: Mar. 21, 2018

(65) Prior Publication Data
US 2019/0290419 A1 Sep. 26, 2019

(51) Int. Cl.
| | | |
|---|---|---|
| *A61F 2/07* | (2013.01) | |
| *A61F 2/848* | (2013.01) | |
| *A61B 17/064* | (2006.01) | |
| *A61B 17/068* | (2006.01) | |
| *A61F 2/844* | (2013.01) | |
| *A61B 17/04* | (2006.01) | |

(Continued)

(52) U.S. Cl.
CPC .............. *A61F 2/07* (2013.01); *A61B 17/064* (2013.01); *A61B 17/068* (2013.01); *A61F 2/848* (2013.01); *A61B 17/10* (2013.01); *A61B 2017/00477* (2013.01); *A61B 2017/00818* (2013.01); *A61B 2017/00862* (2013.01); *A61B 2017/0419* (2013.01); *A61B 2017/0645* (2013.01); *A61F 2/844* (2013.01); *A61F 2002/075* (2013.01)

(58) Field of Classification Search
CPC .. A61B 2017/0419; A61B 17/12–1227; A61B 17/064–2017/0649; A61B 17/08–2017/088; A61B 17/057–2017/00676; A61B 2017/0417; A61F 2/848–2002/8486; A61F 2002/075
See application file for complete search history.

(56) References Cited

U.S. PATENT DOCUMENTS

| | | | | |
|---|---|---|---|---|
| 4,448,194 A | * | 5/1984 | DiGiovanni | A61B 17/0491 112/80.05 |
| 6,152,935 A | * | 11/2000 | Kammerer | A61B 17/0469 606/144 |

(Continued)

FOREIGN PATENT DOCUMENTS

WO 2009143227 A1 11/2009

OTHER PUBLICATIONS

EP19163445.0, Extended European Search Report, 8pgs, dated Aug. 20, 2019.

*Primary Examiner* — Tan-Uyen T Ho
*Assistant Examiner* — Charles M Wei

(57) ABSTRACT

A method of anchoring a prosthesis includes deploying the prosthesis in a vessel. A delivery system including an anchor constrained within a delivery sheath is advanced to the prosthesis. The prosthesis and a vessel wall of the vessel are penetrated with a leading tip of an exterior tine of the anchor, wherein the exterior tine unfolds upon passing through the prosthesis and the vessel wall. An interior tine is deployed within the prosthesis and vessel wall. In the final deployed state, the exterior tine is exterior to and adjacent the vessel wall, the interior tine is interior to and adjacent the prosthesis, and a tine connector of the anchor extends through the vessel wall and the prosthesis.

15 Claims, 10 Drawing Sheets

(51) Int. Cl.
 *A61B 17/10* (2006.01)
 *A61B 17/00* (2006.01)

(56) References Cited

U.S. PATENT DOCUMENTS

| | | | | |
|---|---|---|---|---|
| 7,632,313 | B2* | 12/2009 | Bhatnagar | A61B 17/0642 623/17.11 |
| 7,645,286 | B2 | 1/2010 | Catanese, III et al. | |
| 8,211,124 | B2* | 7/2012 | Ainsworth | A61B 17/0057 606/142 |
| 2001/0010005 | A1* | 7/2001 | Kammerer | A61B 17/064 606/151 |
| 2004/0049211 | A1* | 3/2004 | Tremulis | A61B 17/0401 606/153 |
| 2004/0153102 | A1* | 8/2004 | Therin | A61B 17/0401 606/144 |
| 2005/0187565 | A1* | 8/2005 | Baker | A61B 17/0401 606/151 |
| 2005/0251160 | A1* | 11/2005 | Saadat | A61B 17/0401 606/153 |
| 2005/0288708 | A1* | 12/2005 | Kammerer | A61B 17/0644 606/221 |
| 2007/0049970 | A1* | 3/2007 | Belef | A61B 17/0057 606/232 |
| 2007/0073316 | A1 | 3/2007 | Sgro et al. | |
| 2009/0093824 | A1* | 4/2009 | Hasan | A61B 17/0401 606/139 |
| 2009/0163934 | A1* | 6/2009 | Raschdorf, Jr. | A61B 17/00234 606/139 |
| 2011/0040326 | A1* | 2/2011 | Wei | A61B 17/0401 606/232 |
| 2011/0144423 | A1* | 6/2011 | Tong | A61B 17/0401 600/37 |
| 2012/0059394 | A1* | 3/2012 | Brenner | A61B 1/00087 606/142 |
| 2013/0296639 | A1* | 11/2013 | Lamson | A61B 17/0401 600/30 |
| 2017/0086882 | A1 | 3/2017 | Pereira et al. | |
| 2017/0156723 | A1* | 6/2017 | Keating | A61B 17/0401 |

\* cited by examiner

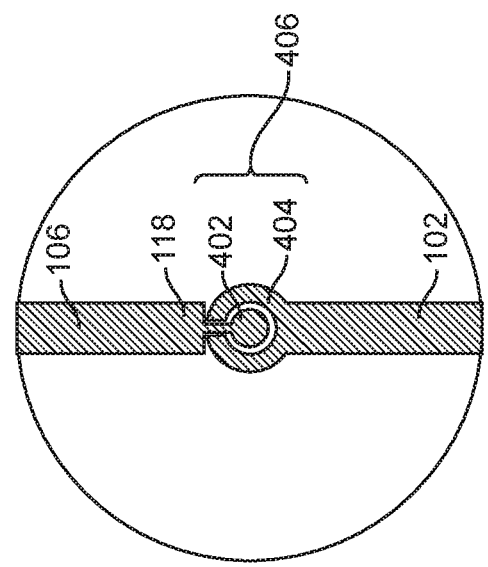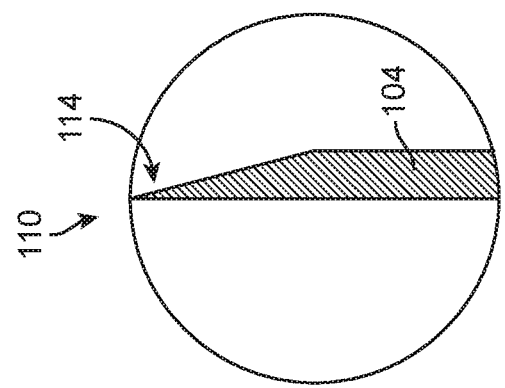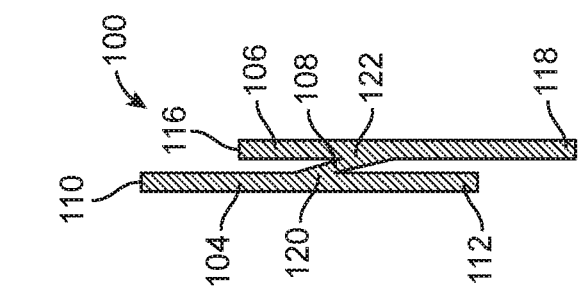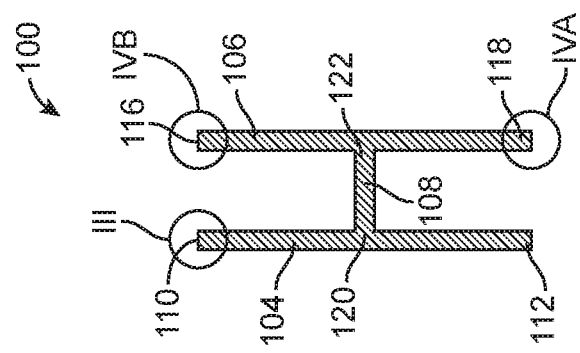
FIG. 4A
FIG. 3
FIG. 2
FIG. 1

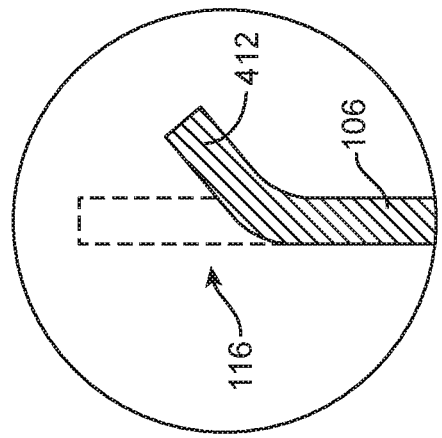
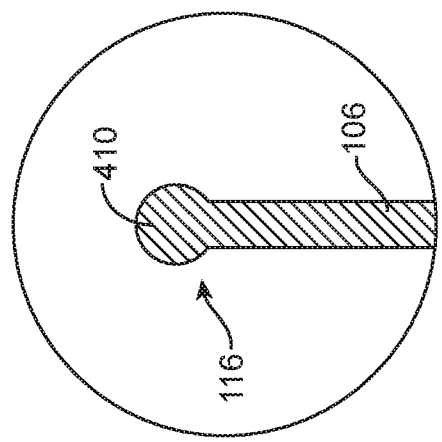
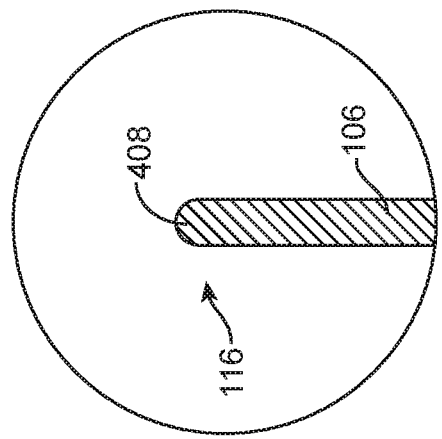

STENT MIGRATION DEVICE AND METHOD

BACKGROUND

Field

The present application relates to an intra-vascular device and method. More particularly, the present application relates to a device for treatment of intra-vascular diseases.

Description of the Related Art

A conventional stent-graft typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

Stent-grafts can migrate from the intended implant location and can also foreshorten over time. To avoid these complications, stent-grafts are sutured to the vessel wall by surgically opening a patient.

SUMMARY

In accordance with one embodiment, a method of anchoring a prosthesis includes deploying the prosthesis in a vessel. A delivery system including an anchor constrained within a delivery sheath is advanced to the prosthesis. The prosthesis and a vessel wall of the vessel are penetrated with a leading tip of an exterior tine of the anchor, wherein the exterior tine unfolds upon passing through the prosthesis and the vessel wall. An interior tine is deployed within the prosthesis and vessel wall. In the final deployed state, the exterior tine is exterior to and adjacent the vessel wall, the interior tine is interior to and adjacent the prosthesis, and a tine connector of the anchor extends through the vessel wall and the prosthesis.

The anchor anchors the prosthesis to the vessel wall. This prevents migration and foreshortening, e.g., in vivo, of the prosthesis.

Embodiments are best understood by reference to the following detailed description when read in conjunction with the accompanying drawings.

BRIEF DESCRIPTION OF DRAWINGS

FIG. 1 is a side perspective view of an anchor in a relaxed and deployed state in accordance with one embodiment.

FIG. 2 is a side perspective view of the anchor in a compressed and pre-deployment state in accordance with one embodiment.

FIG. 3 is an enlarged side view of a region III of the anchor of FIG. 1 in accordance with one embodiment.

FIG. 4A is an enlarged side view of a region IVA of the anchor of FIG. 1 engaged with a pushrod in accordance with one embodiment.

FIGS. 4B1, 4B2, 4B3 are enlarged side views of a region IVB of the anchor of FIG. 1 in accordance with various embodiments.

Common reference numerals are used throughout the drawings and detailed description to indicate like elements.

DETAILED DESCRIPTION

Figure 5:
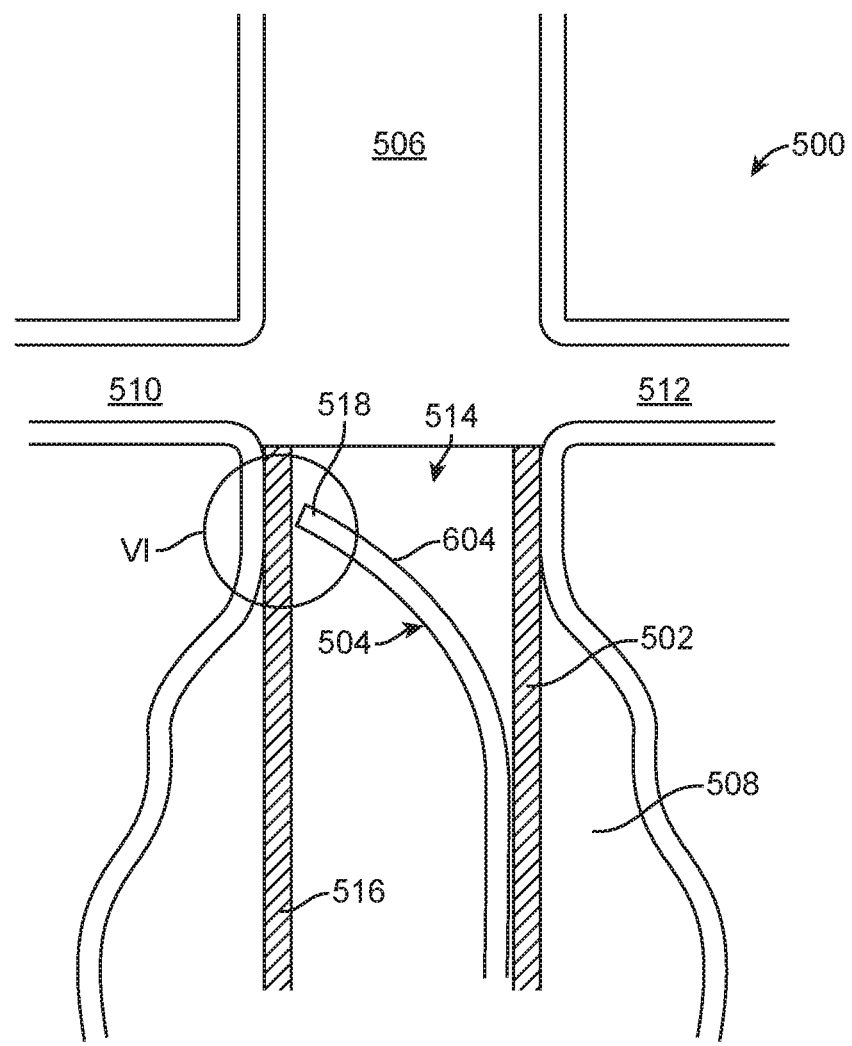
FIG. 5 is a partial cross-sectional view of a vessel assembly including an aneurysm exclusion stent-graft and an anchor delivery system for delivering the anchor of FIGS. 1 and 2 in accordance with one embodiment.
Figure 7:
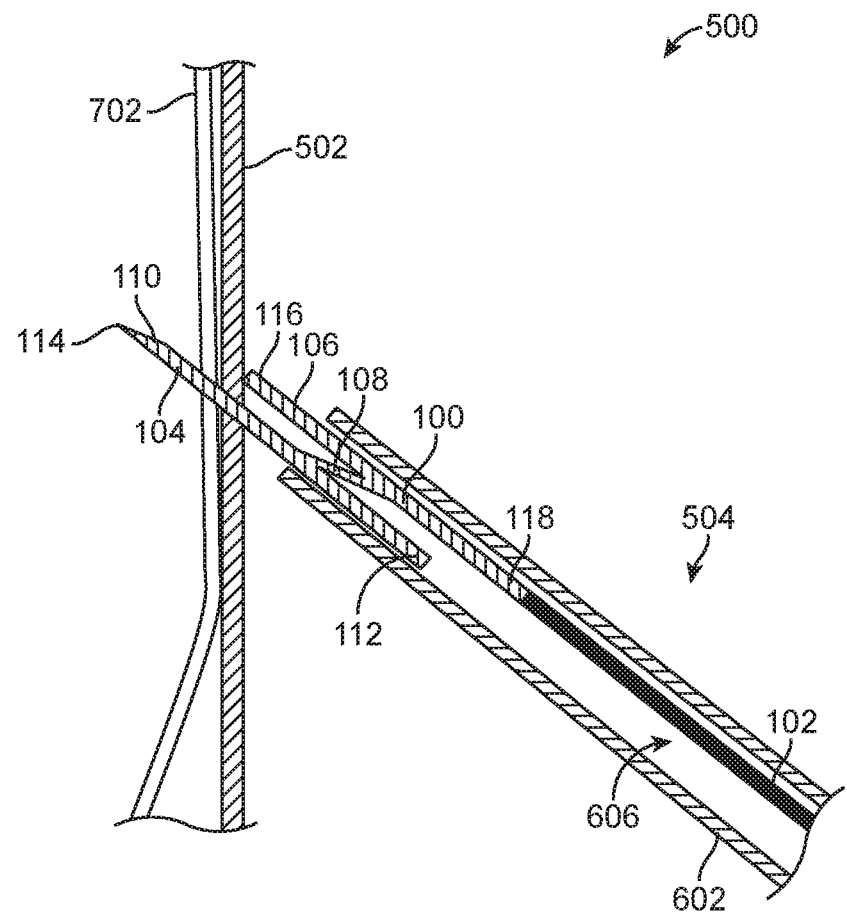
FIGS. 7, 8, and 9 are side views of the vessel assembly of FIG. 6 at later stages during deployment of the anchor in accordance with one embodiment.
Figure 8:
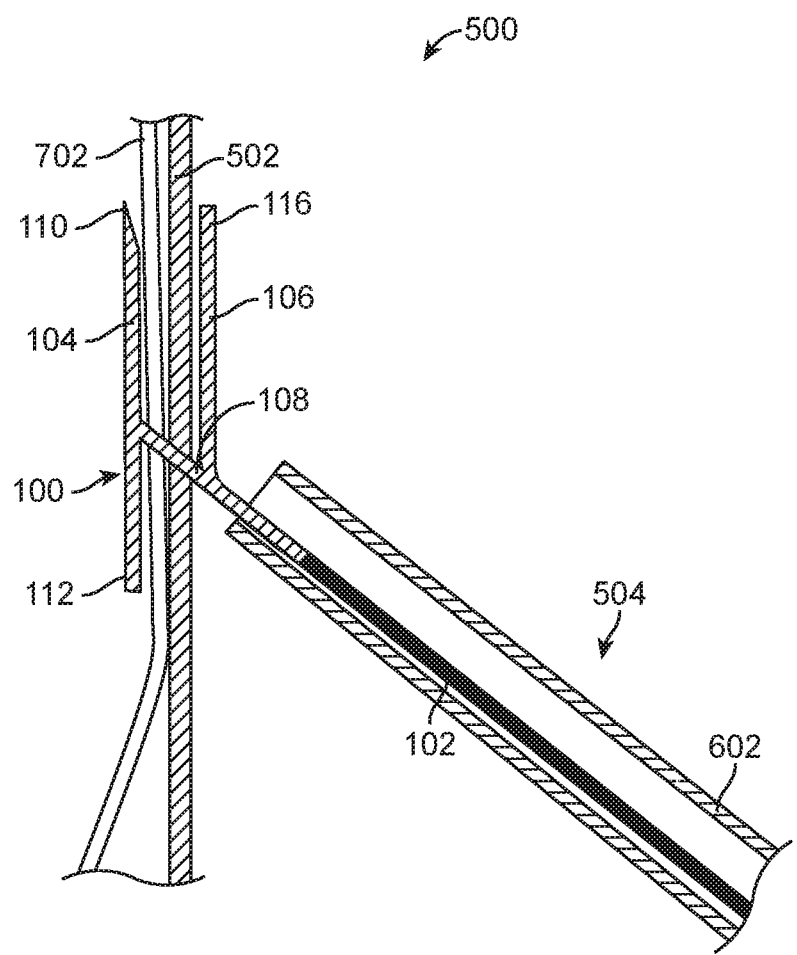
Figure 9:
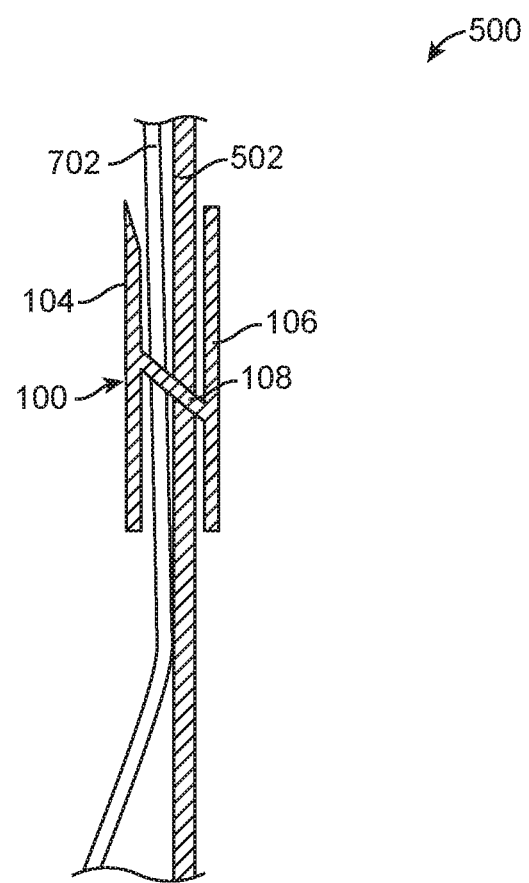

As an overview and in accordance with one embodiment, referring to FIGS. 5 and 7 together, a method of anchoring a prosthesis 502 includes deploying prosthesis 502 in a vessel 506. A delivery system 504 including an anchor 100 constrained within a delivery sheath 602 is advanced to prosthesis 502. Prosthesis 502 and a vessel wall 702 of vessel 506 are penetrated with a leading tip 110 of an exterior tine 104 of anchor 100. Referring now to FIG. 8, exterior tine 104 unfolds upon passing through prosthesis 502 and vessel wall 702. Referring now to FIGS. 8 and 9 together, an interior tine 106 of anchor 100 is deployed within prosthesis 502 and vessel wall 702. In the final deployed state as shown in FIG. 9, exterior tine 104 is exterior to and adjacent vessel wall 702, interior tine 106 is interior to and adjacent prosthesis 502, and a tine connector 108 of anchor 100 extends through vessel wall 702 and prosthesis 502.

Anchor 100 anchors prosthesis 502 to vessel wall 702 and more generally to primary vessel 506. This prevents migration and foreshortening, e.g., in vivo, of prosthesis 502. Prosthesis 502 is secured to vessel wall 702 by anchor 100 without open surgery. By increasing confidence in the securement and use of prosthesis 502, prosthesis 502 can be used in applications otherwise not possible or feasible.

Now in more detail, FIG. 1 is a side perspective view of an anchor 100 in a relaxed and deployed state in accordance with one embodiment. FIG. 2 is a side perspective view of anchor 100 in a compressed and pre-deployment state in accordance with one embodiment. FIG. 3 is an enlarged side view of a region III of anchor 100 of FIG. 1 in accordance with one embodiment. FIG. 4A is an enlarged side view of a region IVA of anchor 100 of FIG. 1 engaged with a pushrod 102 in accordance with one embodiment. Pushrod 102 is not illustrated in FIG. 1.

Referring now to FIGS. 1 through 4A together, anchor 100 includes an exterior tine 104, and interior tine 106, and a tine connector 108. In one embodiment, exterior tine 104, interior tine 106, and tine connector 108 are cylindrical structures, e.g., rods having a length greater than a width. However, in other embodiments, exterior tine 104, interior tine 106, and tine connector 108 have other shapes, for example, are rectangular or oval.

Exterior tine 104 includes a lead tip 110 and a rear tip 112. Exterior tine 104 extends between lead tip 110 and rear tip 112. In accord with this embodiment, lead tip 110 includes a sharp point 114 similar to the point of a pin. However, in other embodiments, lead tip 110 is blunt.

Interior tine 106 includes a lead tip 116 and a rear tip 118. Interior tine 106 extends between lead tip 116 and rear tip 118. In one embodiment, the length of interior tine 106, e.g., the distance between lead tip 116 and rear tip 118, is equal to the length of exterior tine 104, e.g., the distance between lead tip 110 and rear tip 112. However, in other embodiments, exterior tine 104 and interior tine 106 have different lengths and/or different shapes.

Tine connector 108 includes exterior tine end 120 and an interior tine end 122. Exterior tine end 120 is connected to exterior tine 104 between lead tip 110 and rear tip 112, e.g., in the middle of exterior tine 104. Similarly, interior tine end 122 is connected to interior tine 106 between lead tip 116 and rear tip 118, e.g., in the middle of interior tine 106.

When anchor 100 is in its relaxed state as illustrated in FIG. 1, exterior tine 104 and interior tine 106 are parallel to one another. In other embodiments, exterior tine 104 and interior tine 106 extend in different directions but lie within planes parallel to one another or have other orientations. Tine connector 108 is perpendicular to exterior tine 104 and interior tine 106.

Although various features may be discussed as being parallel, perpendicular, or having other relationships, in light of this disclosure, those of skill in the art will understand that the features may not be exactly parallel, perpendicular, etc., but only substantially parallel, perpendicular, etc., e.g., to within manufacturing tolerances.

In accordance with this embodiment, anchor 100 is integral, i.e., is a single piece and not a plurality of separate pieces connected together. For example, anchor 100 is formed of a super elastic material, e.g., metal, a metal wire, a polymer, a polymer bead, or other flexible resilient material. As used herein, superelastically deformed means being capable of returning to its original form, sometimes called relaxed (undeformed) state, after being deformed. In one embodiment, anchor 100 is made of a shape memory material such as nickel titanium alloy, sometimes called nitinol.

Anchor 100 can be superelastically deformed and then returns to its original form when released. For example, FIG. 1 illustrates anchor 100 in its relaxed and non-deformed state and FIG. 2 illustrates anchor 100 in a deformed state. Generally, anchor 100 returns to its relaxed state as illustrated in FIG. 1 absent application of force to anchor 100.

When anchor 100 is in a compressed and pre-deployment state as illustrated in FIG. 2, exterior tine 104 and interior tine 106 are pressed together such that the distance between tines 104, 106 is reduced as compared to the relaxed state as shown in FIG. 1. This causes tine connector 108 and/or tines 104, 106 to deform. For example, tine connector 108 extends at an angle from tines 104, 106. When released, anchor 100 returns from the compressed and pre-deployment state as illustrated in FIG. 2 to the relaxed state as illustrated in FIG. 1.

Paying particular attention now to FIG. 4A, in one embodiment, rear tip 118 of interior tine 106 includes a pushrod connection feature 402 and pushrod 102 includes an anchor connection feature 404 complementary to pushrod connection feature 402. Pushrod connection feature 402 and anchor connection feature 404 are releasably coupled to one another allowing anchor 100 to be selectively released from pushrod 102. Generally, pushrod connection feature 402 and anchor connection feature 404 collectively define a releasable anchor coupling 406 between anchor 100 and pushrod 102.

In accordance with this particular embodiment, pushrod connection feature 402 is a ball and anchor connection feature 404 is a socket containing pushrod connection feature 402 therein. Anchor connection feature 404 is held in a compressed state around pushrod connection feature 402, e.g., by the delivery sheath. When released, e.g., upon exiting the delivery sheath, anchor connection feature 404 expands thus releasing pushrod connection feature 402. In other embodiments, pushrod connection feature 402 and anchor connection feature 404 are a complimentary lock and key structure interconnected with one another.

Although one example of anchor coupling 406 is provided, in other embodiments, other releasable couplings between anchor 100 and pushrod 102 are used. For example, anchor coupling 406 is similar to a connection between a pushrod and an embolic coil. In yet another embodiment, there is no direct connection between anchor 100 and pushrod 102, e.g., pushrod 102 simply pushes on anchor 100 during deployment.

FIGS. 4B1, 4B2, 4B3 are enlarged side views of a region IVB of anchor 100 of FIG. 1 in accordance with various embodiments. Paying particular attention now to FIG. 4B1, in one embodiment, lead tip 116 of interior tine 106 includes a rounded end 408. Rounded end 408 is a smooth curve and includes no corners or sharp edges. Accordingly, rounded end 408 does not dig into a vessel or prosthesis during delivery.

Paying particular attention now to FIG. 4B2, in another embodiment, lead tip 116 of interior tine 106 includes a ball end 410. Ball end 410 is a ball and includes no corners or sharp edges. Accordingly, ball end 410 does not dig into a vessel or prosthesis during delivery. In one embodiment, ball end 410 has a diameter greater than a diameter of interior tine 106.

Paying particular attention now to FIG. 4B3, in yet another embodiment, lead tip 116 of interior tine 106 includes a deflected end 412. Deflected end 412 is a curved end that deflects (curves) away from exterior tine 104 when in the relaxed state, e.g., in the view of FIG. 1. Accordingly, deflected end 412 does not dig into a vessel or prosthesis during delivery as it curves into the vessel when it is extended outside the delivery catheter thus avoiding the vessel. In one embodiment, deflected end 412 is shape memory material such that deflected end 412 can be deformed as indicated by the dashed line in FIG. 4B3 corresponding to the compressed and pre-deployment state of FIG. 2.

Generally, rounded end 408, ball end 410, and deflected end 412 of FIGS. 4B1, 4B2, 4B3, respectively, are referred to as a non-penetration feature.

FIG. 5 is a partial cross-sectional view of a vessel assembly 500 including an aneurysm exclusion stent-graft 502 and an anchor delivery system 504 for delivering anchor 100 of FIGS. 1 and 2 in accordance with one embodiment. Referring now to FIG. 5, a primary vessel 506, e.g., the aorta, includes an aneurysm 508.

Emanating from primary vessel 506 is a first branch vessel 510 and a second branch vessel 512, sometimes called visceral branches of the abdominal aorta. The location of branch vessels 510, 512 vary from patient to patient. Examples of branch vessels 510, 512 include the renal arteries (RA).

Aneurysm exclusion stent-graft 502 is deployed into primary vessel 506 to exclude aneurysm 508 using any one of a number of techniques well known to those of skill in the art. Aneurysm exclusion stent-graft 502 is deployed distal to branch vessels 510, 512 and thus exposes and maintains perfusion of branch vessels 510, 512. In other embodiments, aneurysm exclusion stent-graft 502 covers one or more of branch vessels 510, 512 and has openings and or other structures to maintain perfusion of branch vessels 510, 512. In either embodiment, once anchored within primary vessel 506, blood flows through a lumen 514 of aneurysm exclusion stent-graft 502 thus excluding aneurysm 508.

In one embodiment, aneurysm exclusion stent-graft 502, sometimes generally called a prosthesis 502, includes graft material 516 and one or more stents. Although one example of prosthesis 502 is described, in other embodiments, other prostheses are deployed depending upon the particular application. For example, prosthesis 502 is a stent.

In one embodiment, aneurysm exclusion stent-graft 502 must be anchored to primary vessel 506 to prevent migration of aneurysm exclusion stent-graft 502. For example, aneurysm 508 is a short neck aneurysm having little to no healthy tissue between branch vessels 510, 512 and aneurysm 508. Accordingly, aneurysm exclusion stent-graft 502 is anchored to primary vessel 506 as described below.

Figure 6:
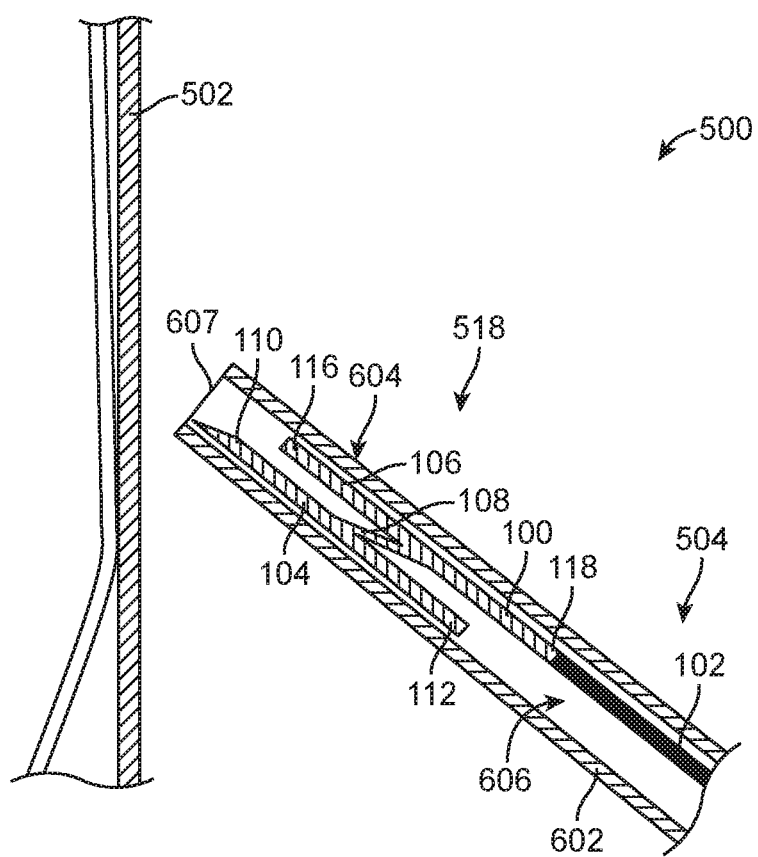
FIG. 6 is an enlarged side view of a region VI of the vessel assembly of FIG. 5 in accordance with one embodiment.

FIG. 6 is an enlarged side view of a region VI of vessel assembly 500 of FIG. 5 in accordance with one embodiment. Referring now to FIGS. 5 and 6 together, anchor delivery system 504 is advanced to the location of aneurysm exclusion stent-graft 502. A distal end 518 of anchor delivery system 504 is aligned with and adjacent aneurysm exclusion stent-graft 502 at a location where anchor 100 is to be deployed.

As used herein, the proximal end of a prosthesis such as aneurysm exclusion stent-graft 502 is the end closest to the heart via the path of blood flow whereas the distal end is the end furthest away from the heart during deployment. In contrast and of note, the distal end of the delivery system such as anchor delivery system 504 is usually identified to the end that is farthest from the operator (handle) while the proximal end of the delivery system is the end nearest the operator (handle). However, those of skill in the art will understand that depending upon the access location, the prosthesis and delivery system description may be consistent or opposite in actual usage.

In FIG. 6, anchor delivery system 504 is illustrated in cross-section to allow visualization of the features therein. Anchor delivering system 504 includes a delivery sheath 602, sometimes called a catheter. Illustratively, delivery sheath 602 is steerable, e.g., is a deflectable catheter, or has a curved distal end 604, e.g., a heat set curve, to allow distal end 604 to point at the location where anchor 100 is to be deployed. Delivery sheath 602 directs anchor 100 toward primary vessel 506.

Distal end 604 is slightly spaced apart from aneurysm exclusion stent-graft 502. In another embodiment, distal end 604 contacts and presses on aneurysm exclusion stent-graft 502. Distal end 604 can include one or more radiopaque markers to allow visualization of the location of distal end 604 and/or is partially or completely radiopaque.

Delivery sheath 602 is a hollow tube and includes an anchor delivery lumen 606 therein. Anchor 100 is compressed and constrained within anchor delivery lumen 606 with leading tip 110 of exterior tine 104 being the most distal part of anchor 100 and pointing outward of delivery sheath 602 and towards a distal sheath opening 607 of delivery sheath 602. Pushrod 102 extends through anchor delivery lumen 606 and pushes anchor 100, e.g., at rear tip 118 of interior tine 106. Generally, anchor 100 is held in the compressed and pre-deployment state such as that illustrated in FIG. 2 within anchor delivery lumen 606.

FIG. 7 is a side view of vessel assembly 500 of FIG. 6 at a later stage during deployment of anchor 100 in accordance with one embodiment. Referring now to FIGS. 5, 6, and 7 together, anchor 100 is advanced out of delivery sheath 602. More particularly, anchor 100 is pushed by pushrod 102 to exit delivery sheath 602. Leading tip 110 of exterior tine 104 contacts and penetrates aneurysm exclusion stent-graft 502 and a vessel wall 702 of primary vessel 506. As discussed above in reference to FIG. 3, in one embodiment, leading tip 110 of exterior tine 104 includes a sharp point 114 facilitating penetration of aneurysm exclusion stent-graft 502 and vessel wall 702.

FIG. 8 is a side view of vessel assembly 500 of FIG. 7 at a later stage during deployment of anchor 100 in accordance with one embodiment. Referring now to FIGS. 5, 7, and 8 together, anchor 100 is further advanced out of delivery sheath 602. More particularly, anchor 100 is further pushed by pushrod 102. This causes exterior tine 104 to completely pass through aneurysm exclusion stent-graft 502 and vessel wall 702. After passing through aneurysm exclusion stent-graft 502 and vessel wall 702, exterior tine 104 of anchor 100 returns to its relaxed state. In its final deployed state, exterior tine 104 is exterior to and adjacent vessel wall 702.

Tine connector 108 extends from exterior tine 104 through vessel wall 702 and aneurysm exclusion stent-graft 502. Interior tine 106 does not penetrate aneurysm exclusion stent-graft 502. For example, leading tip 116 is blunt to prevent leading tip 116 from penetrating aneurysm exclusion stent-graft 502 but to slide thereon as illustrated in the view of FIG. 8. For example, leading tip 116 includes a rounded end 408, a ball end 410, or a deflected end 412 as discussed above in reference to FIGS. 4B1, 4B2, 4B3, respectively. In another embodiment, the length of tine connector 108 is sufficient to allow exterior tine 104 to completely pass through aneurysm exclusion stent-graft 502 and vessel wall 702 without causing contact of interior tine 106 and aneurysm exclusion stent-graft 502.

FIG. 9 is a side view of vessel assembly 500 of FIG. 8 at a final stage during deployment of anchor 100 in accordance with one embodiment. Referring now to FIGS. 5, 8, and 9 together, anchor 100 has been deployed from delivery sheath 602 and separated from anchor delivery system 504. In one embodiment, as pushrod 102 exits delivery sheath 602, pushrod 102 releases anchor 100, for example, as described above in reference to FIG. 4A. Interior tine 106 folds out inside primary vessel 506 and aneurysm exclusion stent-graft 502.

In its final deployed condition as illustrated in FIG. 9, anchor 100 returns to its relaxed state. Exterior tine 104 is exterior to and adjacent vessel wall 702, interior tine 106 is interior to and adjacent aneurysm exclusion stent-graft 502, and tine connector 108 extends through vessel wall 702 and aneurysm exclusion stent-graft 502.

Anchor 100 anchors aneurysm exclusion stent-graft 502 to vessel wall 702 and more generally to primary vessel 506. This prevents migration and foreshortening, e.g., in vivo, of aneurysm exclusion stent-graft 502. Aneurysm exclusion stent-graft 502 is secured to vessel wall 702 by anchor 100 without open surgery. By increasing confidence in the securement and use of aneurysm exclusion stent-graft 502, aneurysm exclusion stent-graft 502 can be used in applications otherwise not possible or feasible.

In one embodiment, the operations illustrated in FIGS. 5 through 9 are repeated any one of a number of times to deploy a plurality of anchors 100 at various desired locations of aneurysm exclusion stent-graft 502.

Figure 10:
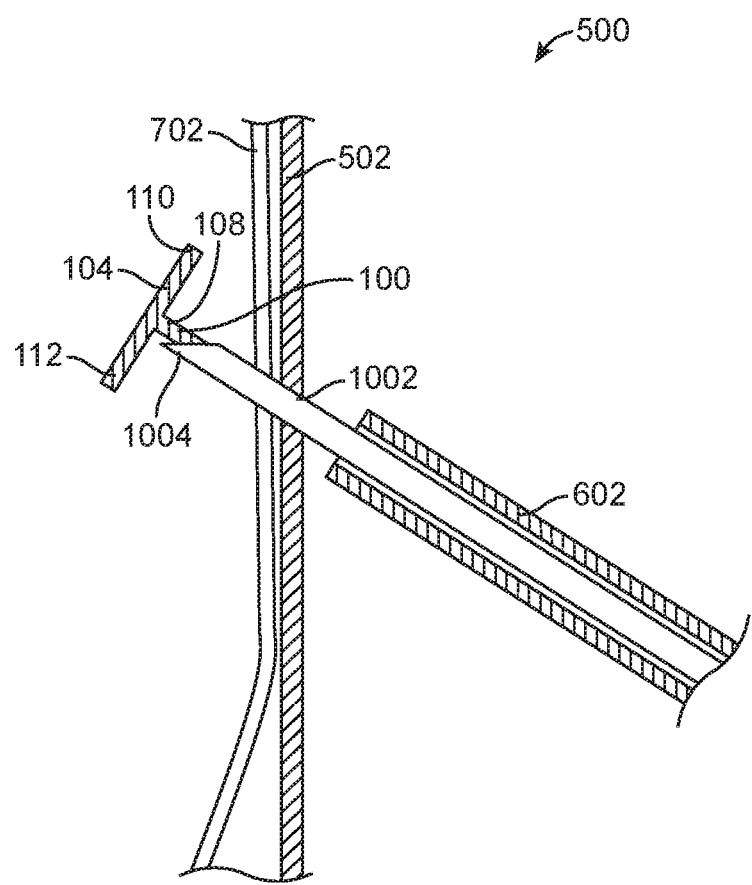
FIG. 10 is an enlarged side view of the region VI of the vessel assembly of FIG. 5 during deployment of the anchor in accordance with another embodiment.

FIG. 10 is an enlarged side view of the region VI of vessel assembly 500 of FIG. 5 during deployment of anchor 100 in accordance with another embodiment. Referring now to FIGS. 1-5 and 10 together, in this embodiment, anchor 100 and pushrod 102 extend through a needle 1002 within sheath 602.

Needle 1002 is a hollow tube similar to a hypodermic needle and includes and anchor delivery lumen therein. During delivery and prior to deployment, anchor 100 is compressed and constrained within the anchor delivery lumen of needle 1002 with leading tip 110 of exterior tine 104 being the most distal part of anchor 100. Pushrod 102 extends through the anchor delivery lumen of needle 1002 and pushes anchor 100, e.g., at rear tip 118 of interior tine 106. Generally, anchor 100 is held in the compressed and pre-deployment state such as that illustrated in FIG. 2 within the anchor delivery lumen of needle 1002.

As illustrated in FIG. 10, needle 1002 is advanced out of delivery sheath 602. In one embodiment, needle 1002 includes a sharp point 1004 facilitating penetration of aneurysm exclusion stent-graft 502 and vessel wall 702 by needle 1002.

After needle 1002 penetrates aneurysm exclusion stent-graft 502 and vessel wall 702, anchor 100 is advanced out of needle 1002. More particularly, anchor 100 is pushed by pushrod 102 to exit needle 1002. This causes exterior tine 104 to completely exit needle 1002. After exiting needle 1002, exterior tine 104 of anchor 100 returns to its relaxed state. In its final deployed state, exterior tine 104 is exterior to and adjacent vessel wall 702.

Figure 11:
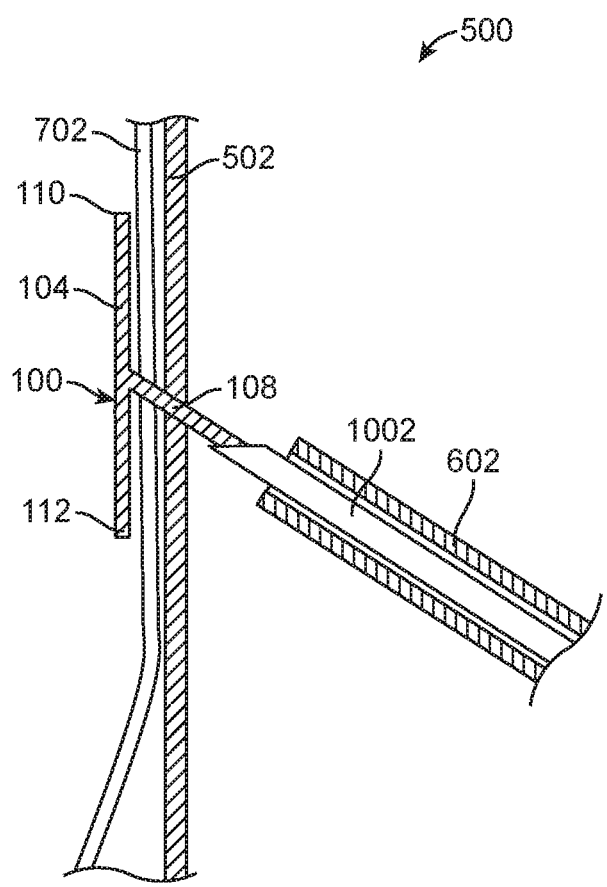
FIGS. 11 and 12 are side views of the vessel assembly of FIG. 10 at later stages during deployment of the anchor in accordance with one embodiment.

FIG. 11 is a side view of vessel assembly 500 of FIG. 10 at a later stage during deployment of anchor 100 in accordance with one embodiment. Referring now to FIGS. 1-5, 10, and 11 together, needle 1002 is withdrawn, i.e., moved proximally, from aneurysm exclusion stent-graft 502 and vessel wall 702 and back into sheath 602. Interior tine 106 of anchor 100 remains within needle 1002 and thus anchor 100 is also moved proximally. This causes exterior tine 104 to contact and stop at vessel wall 702.

As illustrated in FIG. 11, tine connector 108 extends from exterior tine 104 through vessel wall 702 and aneurysm exclusion stent-graft 502. Interior tine 106 is still constrained within needle 1002.

Figure 12:
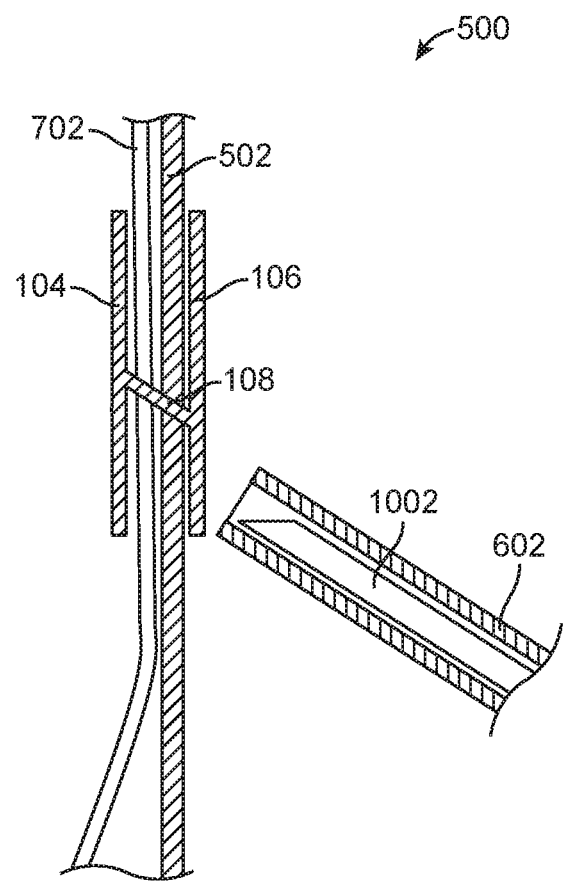

FIG. 12 is a side view of vessel assembly 500 of FIG. 11 at a final stage during deployment of anchor 100 in accordance with one embodiment. Referring now to FIGS. 1-5, 11, and 12 together, interior tine 106 has exited needle 1002. More generally, anchor 100 has been separated from needle 1002.

In one embodiment, pushrod 102 is advanced (moved distally) to advance interior tine 106 from needle 1002. As pushrod 102 exits needle 1002, pushrod 102 releases anchor 100, for example, as described above in reference to FIG. 4A. Interior tine 106 folds out inside primary vessel 506 and aneurysm exclusion stent-graft 502.

In its final deployed condition as illustrated in FIG. 12, anchor 100 returns to its relaxed state. Exterior tine 104 is exterior to and adjacent vessel wall 702, interior tine 106 is interior to and adjacent aneurysm exclusion stent-graft 502, and tine connector 108 extends through vessel wall 702 and aneurysm exclusion stent-graft 502.

Anchor 100 anchors aneurysm exclusion stent-graft 502 to vessel wall 702 and more generally to primary vessel 506. This prevents migration and foreshortening, e.g., in vivo, of aneurysm exclusion stent-graft 502. Aneurysm exclusion stent-graft 502 is secured to vessel wall 702 by anchor 100 without open surgery. By increasing confidence in the securement and use of aneurysm exclusion stent-graft 502, aneurysm exclusion stent-graft 502 can be used in applications otherwise not possible or feasible.

In one embodiment, the operations illustrated in FIGS. 5, 10 through 12 are repeated any one of a number of times to deploy a plurality of anchors 100 at various desired locations of aneurysm exclusion stent-graft 502.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A delivery system comprising:
    an anchor comprising:
        an exterior tine;
        an interior tine comprising a leading tip comprising a non-penetration feature, the non-penetration feature comprising a ball end having a diameter larger than a diameter of the interior tine; and
        a tine connector extending between the exterior tine and the interior tine, the anchor being integral;
        wherein the exterior tine comprises:
            a leading tip comprising a sharp point; and
            a rear tip.

2. The delivery system of claim 1 wherein the tine connector is connected to the exterior tine between the leading tip of the exterior tine and the rear tip.

3. The delivery system of claim 1 wherein the interior tine further comprises:
    a rear tip comprising a pushrod connection feature.

4. The delivery system of claim 3 wherein the tine connector is connected to the interior tine between the leading tip and the rear tip.

5. The delivery system of claim 3 further comprising a pushrod comprising an anchor connection feature releasably coupled to the pushrod connection feature.

6. The delivery system of claim 1 wherein the interior tine further comprises:
    a rear tip.

7. The delivery system of claim 1 further comprising a delivery sheath constraining the anchor.

8. The delivery system of claim 7 wherein the delivery sheath comprises a curved distal end.

9. The delivery system of claim 1 wherein the anchor consisting of a single integral piece of super elastic material.

10. The delivery system of claim 9 wherein when the anchor is in a compressed state, a distance between the exterior tine and the interior tine is reduced as compared to when the anchor is in a relaxed state, wherein the super elastic material is superelastically deformed when in the compressed state, the anchor returning to the relaxed state upon being released from the compressed state.

11. A delivery system for anchoring a prosthesis to a vessel, the delivery system comprising:
    an anchor comprising:
        an exterior tine comprising a leading tip comprising a sharp point configured to penetrate the prosthesis and a vessel wall of the vessel;
        an interior tine comprising a leading tip comprising a non-penetration feature, the non-penetration feature comprising a deflected end that curves away from the exterior tine when the anchor is in a relaxed state; and
        a tine connector extending between the exterior tine and the interior tine.

12. The delivery system of claim 11 further comprising a delivery sheath, the anchor being constrained within a delivery lumen of the delivery sheath with the leading tip of the exterior tine pointing outward towards a distal sheath opening of the delivery sheath.

13. The delivery system of claim 12 further comprising a pushrod within the delivery sheath, the pushrod configured to push the anchor out of the delivery sheath.

14. The delivery system of claim 13 further comprising an anchor coupling releasably coupling the pushrod to the anchor.

15. The delivery system of claim 14 wherein the anchor coupling is configured to release the anchor upon exiting the delivery sheath.

* * * * *